US012211597B2

(12) United States Patent
Cowan et al.

(10) Patent No.: US 12,211,597 B2
(45) Date of Patent: *Jan. 28, 2025

(54) PATIENT INTERACTIVE HEALING ENVIRONMENT

(71) Applicant: CERNER INNOVATION, INC., Kansas City, KS (US)

(72) Inventors: Daniel P. Cowan, Kansas City, MO (US); Christopher M. Ruff, Olathe, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 501 days.

This patent is subject to a terminal disclaimer.

(21) Appl. No.: 17/461,371

(22) Filed: Aug. 30, 2021

(65) Prior Publication Data

US 2021/0391044 A1    Dec. 16, 2021

Related U.S. Application Data

(60) Continuation of application No. 15/394,222, filed on Dec. 29, 2016, now Pat. No. 11,133,089, which is a
(Continued)

(51) Int. Cl.
*G16H 10/60* (2018.01)
*G06F 16/9535* (2019.01)
(Continued)

(52) U.S. Cl.
CPC ......... *G16H 10/60* (2018.01); *G06F 16/9535* (2019.01); *G06Q 10/06* (2013.01);
(Continued)

(58) Field of Classification Search
None
See application file for complete search history.

(56) References Cited

U.S. PATENT DOCUMENTS 5,966,692 A    10/1999 Langer et al.
7,444,291 B1   10/2008 Prasad et al.
(Continued)

FOREIGN PATENT DOCUMENTS

CA    2281835 A1    9/1998

OTHER PUBLICATIONS

Cannon et al., Unpublished U.S. Appl. No. 12/567,956, filed Sep. 28, 2009, titled "Clinician to Device Association".
(Continued)

*Primary Examiner* — Lena Najarian
(74) *Attorney, Agent, or Firm* — Kraguljac Law Group, LLC (57) ABSTRACT

Systems, methods, and computer-readable media for providing an interactive healing environment to a patient are provided. Servers in a network may operate a set of modules to communicate with a client device of the patient. The set of modules may operate to enhance communication between the patient and the healthcare providers of patient in the healthcare facility. The modules may also interact with medical devices associated with the patient. The medical devices may be connected to a component, such as a bus, that receives data from the medical devices and determines where the data should be sent.

20 Claims, 6 Drawing Sheets

Related U.S. Application Data division of application No. 12/553,451, filed on Sep. 3, 2009, now abandoned.

(51) Int. Cl.

| | | |
|---|---|---|
| *G06Q 10/06* | (2023.01) | |
| *G16H 10/20* | (2018.01) | |
| *G16H 10/65* | (2018.01) | |
| *G16H 40/20* | (2018.01) | |
| *G16H 40/67* | (2018.01) | |
| *G16Z 99/00* | (2019.01) | |
| *H04L 67/52* | (2022.01) | |
| *H04L 67/01* | (2022.01) | |

(52) U.S. Cl.
CPC ............ *G16H 10/20* (2018.01); *G16H 10/65* (2018.01); *G16H 40/20* (2018.01); *G16H 40/67* (2018.01); *G16Z 99/00* (2019.02); *H04L 67/52* (2022.05); *H04L 67/01* (2022.05)

(56) References Cited

U.S. PATENT DOCUMENTS

| | | |
|---|---|---|
| 7,716,072 B1 | 5/2010 | Green et al. |
| 2001/0034615 A1 | 10/2001 | Wilkinson et al. |
| 2002/0013516 A1 | 1/2002 | Freyre et al. |
| 2002/0065686 A1 | 5/2002 | Monteleone et al. |
| 2002/0103674 A1 | 8/2002 | Reeder et al. |
| 2002/0104271 A1 | 8/2002 | Gallant |
| 2002/0111831 A1 | 8/2002 | Harada |
| 2002/0120676 A1 | 8/2002 | Biondi et al. |
| 2002/0138338 A1 | 9/2002 | Trauth et al. |
| 2002/0147390 A1 | 10/2002 | Markis et al. |
| 2002/0147782 A1 | 10/2002 | Dimitrova et al. |
| 2002/0187463 A1 | 12/2002 | Aspe et al. |
| 2003/0088290 A1* | 5/2003 | Spinelli ............... G16H 20/30 607/30 |
| 2003/0140928 A1 | 7/2003 | Bui et al. |
| 2004/0039602 A1 | 2/2004 | Greenberg et al. |
| 2004/0176667 A1 | 9/2004 | Mihai et al. |
| 2005/0075904 A1 | 4/2005 | Wager et al. |
| 2005/0124866 A1* | 6/2005 | Elaz ............... A61M 16/0051 128/920 |
| 2005/0133027 A1* | 6/2005 | Elaz ............... A61B 5/002 128/200.24 |
| 2005/0182655 A1 | 8/2005 | Merzlak et al. |
| 2006/0047538 A1 | 3/2006 | Condurso et al. |
| 2006/0069717 A1 | 3/2006 | Mamou et al. |
| 2006/0277066 A1 | 12/2006 | Hungerford et al. |
| 2008/0015903 A1 | 1/2008 | Rodgers |
| 2008/0040628 A1* | 2/2008 | Mandal ............... H04L 43/0817 714/4.1 |
| 2008/0046292 A1 | 2/2008 | Myers et al. |
| 2008/0077031 A1 | 3/2008 | Spinelli et al. |
| 2008/0077447 A1 | 3/2008 | Jung et al. |
| 2008/0126126 A1 | 5/2008 | Ballai |
| 2008/0288279 A1* | 11/2008 | Henley ............... G16H 40/67 705/2 |
| 2008/0319781 A1 | 12/2008 | Stivoric et al. |
| 2009/0099866 A1 | 4/2009 | Newman |
| 2009/0119124 A1 | 5/2009 | Kambaloor |
| 2009/0182594 A1 | 7/2009 | Choubey |
| 2009/0204434 A1 | 8/2009 | Breazeale, Jr. |
| 2009/0222284 A1 | 9/2009 | Mceachern |
| 2010/0010859 A1 | 1/2010 | Ratakonda et al. |
| 2010/0137693 A1 | 6/2010 | Porras et al. |
| 2010/0169121 A1 | 7/2010 | Herbst et al. |
| 2011/0001605 A1 | 1/2011 | Kiani et al. |
| 2011/0054936 A1 | 3/2011 | Cowan et al. |
| 2013/0096936 A1 | 4/2013 | Sampath et al. |
| 2017/0140106 A1 | 5/2017 | Cowan et al. |

OTHER PUBLICATIONS

Herbst et al., Unpublished U.S. Appl. No. 12/347,475, filed Dec. 31, 2008, titled "Patient to Device Association".

Herbst et al., Unpublished U.S. Appl. No. 12/347,487, filed Dec. 31, 2008, titled "Patient to Device Association Based on Suggested Devices".

Nolte et al., Unpublished U.S. Appl. No. 12/567,174, filed Sep. 25, 2009, titled "Processing Event Information of Various Sources".

Nolte et al., Unpublished U.S. Appl. No. 12/641,184, filed Dec. 17, 2009, titled "Gauging Resource Intensiveness of Providing Care to a Patient".

Nolte et al., Unpublished U.S. Appl. No. 13/236,339, filed Sep. 19, 2011, titled "Facilitating and Tracking Clinician-Assignment Status".

Wallace D, R. , "Software Quality Lessons from Medical Device Failure Data", U.S. Department of Commerce Technology Administration Information Technology Laboratory National Institute of Standards and Technology, Nov. 1999.

* cited by examiner

PATIENT INTERACTIVE HEALING ENVIRONMENT

CROSS-REFERENCE TO RELATED APPLICATIONS

This application is a continuation of U.S. application Ser. No. 15/394,222, filed on Dec. 29, 2016, which is a divisional of U.S. application Ser. No. 12/553,451, filed on Sep. 3, 2009, the entirety of which are incorporated herein by reference.

BACKGROUND

Typically, a patient in a healthcare facility spends most of their time confined to a bed without a complete understanding of their care regimen or team of care providers. In many instances, this lack of personal care information may reinforce patient perceptions of helplessness and isolation during treatment at a healthcare facility. The overall unawareness of what is to take place during their stay at the healthcare facility can make patients feel out of control and detached from the care they are receiving. In-patient stays in clinical institutions can be nerve-wracking experiences for many individuals and simple knowledge about the patient's schedule, team of care providers, or information regarding their health record can aid dramatically in easing a patient's mind and reduce a patient's discontent with in-patient stays. The patient hospital experience may be improved by enhancing communication between the patient and the care team and by empowering patients in the management of their healthcare.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention provide systems and methods for providing an interactive healing environment to a patient in a healthcare facility. Servers in a network may operate a set of modules to communicate with a client device of the patient. The set of modules may operate to enhance communication between the patient and the people who give care to the patient in the healthcare facility. Medical devices may be connected to a component, such as a bus, that receives data from the medical devices and determines where the data should be sent. This data may be published by the bus, in one instance, to the patient's electronic medical record, may be routed to a data store so that the data can be archived and queried by a healthcare provider in the future, and may also be retrieved by the operating the set of modules and selectively presented to the patient by way of a client device. Data may be continuously received from a particular medical device during a period of time that the medical device is connected to the bus, or a component therein. The client device of the patient may operate to provide an interactive interface between the patient and the set of modules in the servers.

More particularly, a first aspect of an embodiment of the present invention is directed toward a system for providing an interactive healing environment to a patient in a healthcare facility. The system includes various components, including servers operating in a private network, each server having a processor coupled to a memory for operating a set of modules to communicate with a client device of the patient. The set of modules includes an information module that provides a set of information about the healthcare facility; a care team module that provides a set of information about people who give care to the patient in the healthcare facility; and an education module that provides at least one of a health education information, an electronic document retrieval, and an interactive patient education. Further, the set of modules includes a scheduling module that provides at least one of a schedule for the patient and a task list for the patient; a health records module that provides the patient access to at least one of their personal care information and their personal health record provider; and a treatment module that provides real-time information from medical devices associated with the patient. The medical devices operate to treat the patient or operate to support the patient. The client device operates to provide an interactive interface between the patient and the set of modules in the servers.

In a second aspect, embodiments of the present invention take the form of computer-readable storage media having computer-executable instructions embodied thereon, that, when executed perform a method for providing an interactive healing environment to a patient. Initially, the method involves receiving an identification of the patient, receiving an identification of medical devices, and associating the patient, the medical devices, and a set of healthcare services provided by a healthcare facility to one another for a period of time determined by a treatment of the patient in the healthcare facility. The method further includes customizing a set of system services that are accessed by the patient. The set of system services enables the patient to interact with a set of modules that include at least one of an information module, a care team module, an education module, a scheduling module, a health records module and a treatment module. The set of system services is provided to a client device. The patient retrieves and inputs information by using the set of system services.

A further aspect of an embodiment of the present invention takes the form of computer-storage media having computer-executable instructions embodied thereon, that, when executed perform a method for providing an interactive healing environment to a patient The method includes, operating servers in a private network. Each server has a processor coupled to a memory. The servers operate a set of modules. The set of modules communicates with a client device of the patient. The set of modules includes an information module that provides a set of information about the healthcare facility; a care team module that provides a set of information about people who give care to the patient in the healthcare facility; an education module that provides at least one of a health education information, an electronic document retrieval, and an interactive patient education; a scheduling module that provides at least one of a schedule for the patient and a task list for the patient; a health records module that provides the patient access to at least one of their personal care information and their personal health record; and a treatment module that provides real-time information from medical devices associated with the patient. The method further includes retrieving data from medical devices. The medical devices operate to treat the patient or operate to support the patient. The retrieved data is stored on the servers. The client device is used to provide an interactive interface between the patient and the set of modules in the servers.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide systems, methods, and computer-readable media for, among other things, providing an interactive healing environment to a patient in a healthcare facility. Initially, a healthcare facility may be any hospital, doctor's office or facility where patients are treated. An interactive healing environment may include a combination of hardware components and software applications that provide comprehensive communication, education and entertainment for patients within a healthcare facility.

Servers in a network may operate a set of modules to communicate with a client device of the patient. The set of modules may operate to enhance communication between the patient and a healthcare provider. As used herein, the term "healthcare provider" or "provider" refers to the people who provide healthcare services to the patient in the healthcare facility. Healthcare providers may include clinicians. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like.

Medical devices may be connected to a component, such as a bus, that receives data from the medical devices and determines where the data should be sent. A medical device may be any device, stationary or otherwise, that may be used to treat a patient in a hospital, doctor's office, etc. For exemplary purposes only and not limitation, medical devices may include monitors, ventilators, pumps (e.g., infusion pumps, balloon pumps), a patient's bed, sequential compression devices, electronic security devices, and the like. Some medical devices may be capable of being associated with orders, such as a patient's bed (e.g., order compliance data for a falls risk patient including head rails up and head angle of the bed), and others may not, such as monitors, ventilators, etc. Orders are typically given or made by clinicians who are authorized to give such orders, and may vary depending on the patient, or by type of device required, if any, to carry out a particular order.

Initially, patients, medical devices, and orders for healthcare services provided by the healthcare facility may be identified in a number of ways, such as by scanning a barcode corresponding to the patient, device, or order; entering some type of identification corresponding to the patient, device; or order into a computing device (e.g., PDA or other handheld computing device), or searching an electronically searchable database that contains a plurality of identifications corresponding to patients, devices, and orders. Orders may be associated to patients, as orders are typically made for a particular patient.

The data received from the one or more medical devices may be published by the bus, in one instance, to the patient's electronic medical record or may be routed to a data store so that the data can be archived and queried by a healthcare provider in the future. In various embodiments of the present invention, data from various medical devices may be transferred or routed to a patient's electronic medical record (EMR). As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare.

The data may also be retrieved by the one or more severs operating the set of modules and selectively presented to the patient via the client device. Data may be continuously received from a particular medical device during a period of time that the medical device is connected to the bus, or a component therein. The client device of the patient may operate to provide an interactive interface between the patient and the set of modules in the one of more servers.

Having briefly described embodiments of the present invention, an exemplary operating environment suitable for use in implementing embodiments of the present invention is described below.

Figure 1:
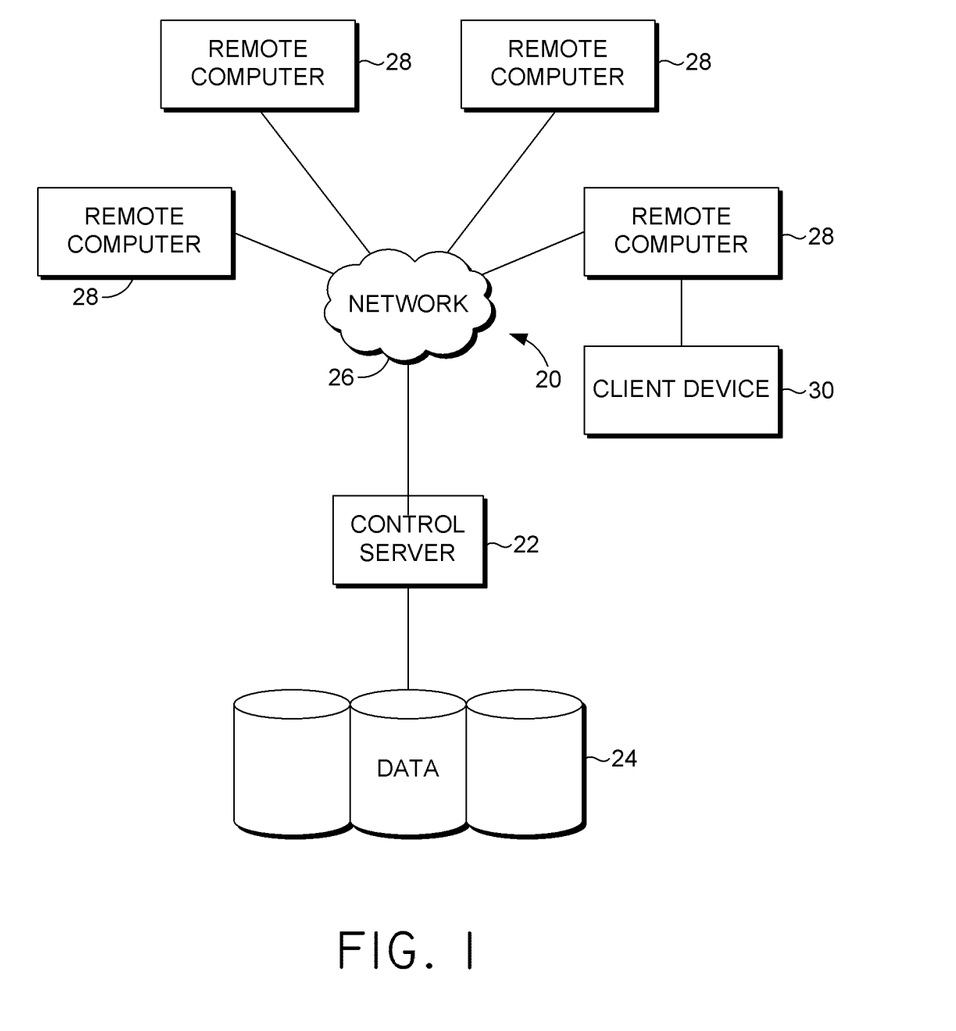
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer. Furthermore, remote computer 28 may include an output to a client device 30, the client device 30 may operate to provide an interactive interface between the patient and the set of modules in the control server 22. As used herein, the term client device refers to a computing device that is accessibly by the in-patient, the family members and/or friends of the in-patient and the like. The client device may include a display device attached to it. Embodiments of the present invention contemplate that information pertaining to the patient may be views by individuals outside of the healthcare facility, for instance, the information may be viewable by a family member at his or her place of residence. Client device 30 may include a flat panel monitor having an interactive touch screen located in proximity to the patient and readily available to the patient and the patient's family members/friends at all time. For example, client device 30 may include a bedside unit that uses a touch screen personal computer mounted on an articulating arm or a flat screen television mounted on a footwall.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
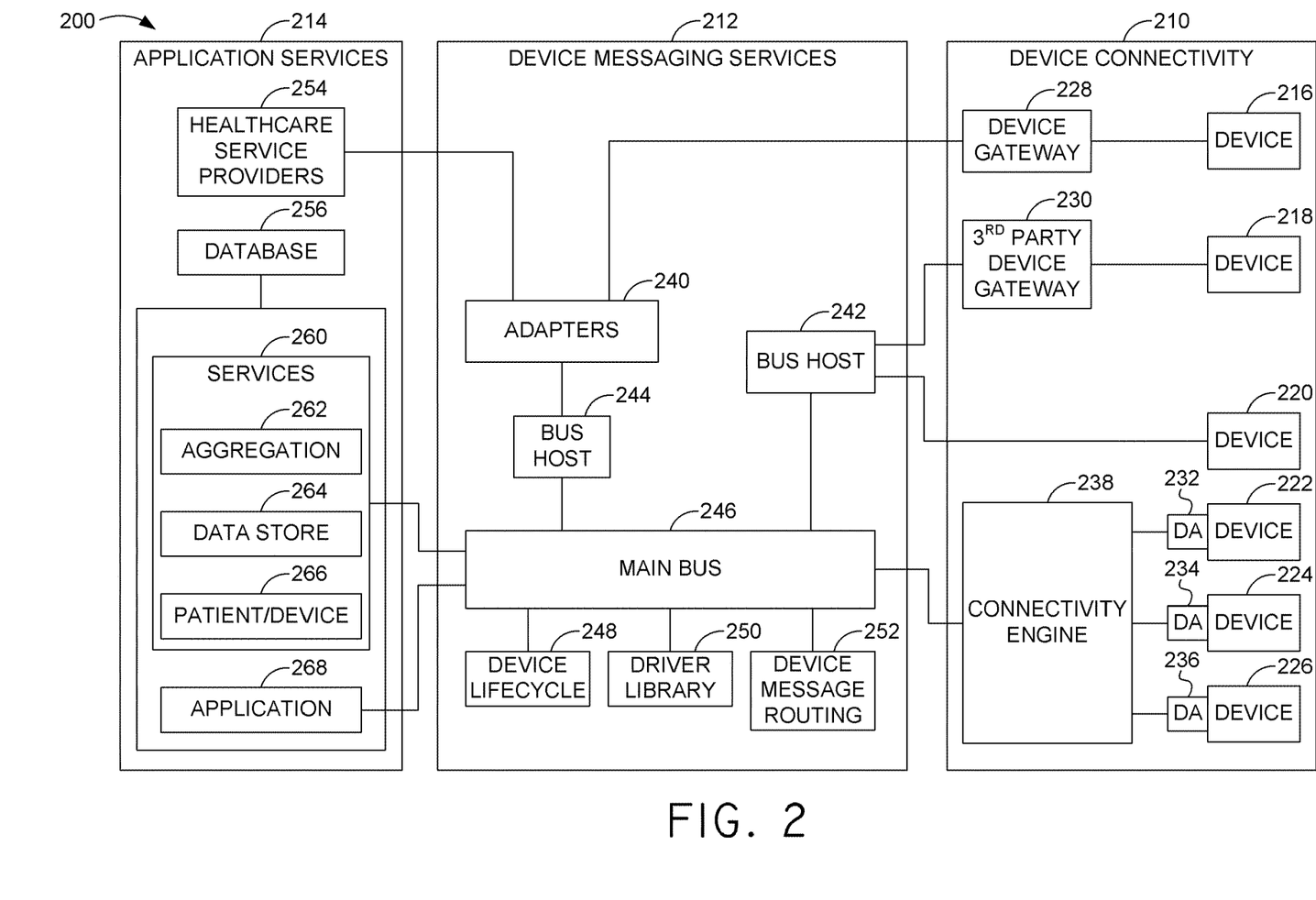
FIG. 2 is an exemplary system architecture suitable for use in implementing embodiments of the present invention.

FIG. 2 is an exemplary system architecture 200 suitable for use in implementing embodiments of the present invention. Generally, the exemplary system architecture 200 advantageously allows for communication with medical devices, for example, through a bus or server, instead of communication directly with the medical devices. A patient to device association may be initiated, and the existence of a bus or server may assist in maintaining that association until the occurrence of a disassociation event. If a computing device, such as a PDA, for example, were to communicate directly with a medical device, the relationship or association between the patient and medical device may terminate when that particular medical device is no longer being used for that particular patient. There may be instances, however, when a healthcare provider may want the association between that patient and medical device to continue until the occurrence of some disassociation event. In that case, a bus may assist in maintaining and managing that relationship.

Initially, the exemplary system architecture 200 includes device connectivity 210, device messaging services 212, and application services 214. The device connectivity 210 includes one or more medical devices that are connected to the device messaging services 212 such that the devices may, at a later time, be associated to a particular patient and/or an order. These devices may include, but are not limited to monitors, cardiac ventilators, balloon pumps, patient beds, infusion pumps, sequential compression devices, electronic security devices, vital signs devices, or any other device that a health care provider may use for a patient while the patient is in the hospital. These devices are shown in FIG. 2 as items 216, 218, 220, 222, 224, and 226.

Each medical device may communicate with the device messaging services 212 in a different way. For example, some devices, such as device 216, may utilize a device gateway 228. A gateway is generally a device that connects networks or other devices using different communications protocols so that information can be easily passed from one to the other. A gateway may both transfer information and convert it to a form compatible with the protocols used by the receiving network. Here, the device gateway assists in the transfer of data from the device 216 to the device messaging services 212. As will be described in greater detail below, an adapter, such as adapter 240 may be used in instances where the device gateway 228, was provided by the device manufacturer. The adapter 240 is typically used to facilitate communication from a consumer to the gateway over the consumer's protocol. It should be noted that an adapter may reside on or near the device messaging services, or may reside near the actual device or device gateway. In other instances, a device gateway may be a third-party device gateway 230. In these instances, an adapter may not be necessary, as the device messaging services 212 may already know what type of messages to expect from that device 218 through the third-party device gateway 230. Many different connection types may be utilized between devices, gateway servers, and components of the device messaging services 212, including, but not limited to, HL7 TCP/IP, a software development kit (SDK), RS 232, etc.

Other devices, such as device 220, may have an internal gateway or other component such that a gateway like 228 or 230 would not be needed. These devices may have all of the required capability built into it, and, if necessary, may even have their own adapters incorporated therein such that a separate adapter would not be necessary. Still other devices, such as devices 222, 224, and 226, may be legacy devices that are older and don't have networking built-ins. For example, it may not be possible to plug in a CAT 5 network to the legacy devices, the devices may not have wireless networking capabilities, etc. A serial port may be the only connection mechanism that exists on these devices. For these devices, a connectivity engine 238 and device adapters 232, 234, and 236 may be used. The device adapter is a hardware device that is affixed directly onto the medical device, and acts as the sole source of identification and connection to the connectivity engine 238. Device adapters 232, 234, and 236 are configurable with device specific information including, but not limited to, manufacturer, device name, device model, port settings, and the like. Device adapters 232, 234, and 236 may use various connection mechanisms to connect to the connectivity engine 238 including, but not limited to, Universal Serial Bus (USB) or Personal Area Network (PAN). The connectivity engine 238 is a piece of hardware that may be connected to devices 222, 224, and 226 either wirelessly or via a wired connection. Even if there is a wired connection between the connectivity engine 238 and a device, there may still be a wireless connection over a wireless network between the connectivity engine 238 and the device messaging services 212.

The connectivity engine 238 may also assist in detecting types of devices so that the appropriate driver may be loaded, which may be based on the make and model of the particular device. The connectivity engine 238 may be located on the device messaging services 212 or as part of the device subsystems 210, as illustrated in FIG. 2. The device messaging services 212 or a component thereof may communicate with the connectivity engine 238 to establish a connection to the device itself. In one embodiment, the connectivity engine 238 may be physically present in a patient's room so that when a new device, such as a legacy device, is brought into that room, it may be connected to the connectivity engine 238 if needed. At that time, a connect event may occur, and the device messaging services 212 may broadcast the connect event to other components who may need to know.

The medical devices, either directly or indirectly through a gateway, connectivity engine, or other component are connected to the device messaging services 212. The device messaging services 212, in some embodiments, may generally include one or more adapters 240, one or more bus hosts, such as bus hosts 242 and 244, a main bus 246, a device lifecycle 248, a driver library 250, and a device message routing 252. As previously described, an adapter may be used when the device gateway, such as device gateway 228, is provided by the manufacturer of a device, for example. The adapter 240 assists to facilitate communication from a consumer to the gateway over the consumer's protocol. While one adapter 240 is illustrated in FIG. 2, it is contemplated to be within the scope of the present invention that more than one adapter 240 may be used. In one embodiment, one adapter 240 may be used for more than one medical device, but in another embodiment, each medical device requiring an adapter may require a separate adapter. Further, the adapter 240 may be used to communicate data from the device messaging services 212 to healthcare service providers 254. In these cases, the data may not be transferred through any system services or applications, but may be transferred directly to other healthcare service providers 254. Typically, an inbound and outbound adapter would be provided to transform messages to and from a standard format and protocol, such as HL7.

A bus host, such as bus host 242 or 244 may be used to perform several functions, including, but not limited to, detecting hardware that is plugged in or directly connected to the host, loading appropriate device drivers after the device has been identified, dynamically locating and installing drivers if the driver is not currently present on the host, and for unloading the device driver after the device has been disconnected. A bus host may not be utilized for each and every medical device, but may be used for some that don't have device adapters, for example, which perform many of the functions listed above. The embodiment of FIG. 2, for example, has a bus host for devices 216, 218, and 220, which are not shown as having device adapters, such as device adapters 232, 234, and 236, nor do they require use of the connectivity engine 238. In addition to the above described functionality of the bus hosts 242 and 244, they may also allow for communication to the device to get various types of information to and from the device. This information may be, for example, determining whether the bed rails are up or down, or even determining the patient's weight when the patient is sitting or lying on the bed.

The main bus 246 provides connection framework, as it may create and manage all connections to the device messaging services 212. The main bus 246 also provides messaging architecture for the device messaging services 212. The main functionality of the main bus 246 includes providing general operational and management capabilities for connected devices, which may vary depending on the system service that is subscribing or requesting the data from the devices.

A device lifecycle 248 may detect the presence of a device on the main bus 246. The device lifecycle 248 also may maintain an accurate directory of currently connected medical devices to the main bus 246 as various medical devices become connected. Further, it may ensure "active" connectivity of a medical device to the main bus 246 via a device heartbeat. A heartbeat is an indication given at a certain interval of time that a particular medical device is connected to the main bus 246. This interval may vary, and may be regular, such as every 20 seconds, for example. Additionally, the interval may depend on each medical device. As a medical device deregisters, or becomes unconnected to the main bus 246, the device lifecycle 248 may be responsible for sending out a notice of a disconnect event, and will then stop sending that device's heartbeat out to certain components that require that information. There are various phases of the device lifecycle 248, which may include, in one embodiment, a notification phase that notifies of an event generated at the device connection and of a device connected as directly to the main bus 246; an interrogation phase; an identification phase that identifies the vendor, make, model, etc. of each medical device and that finds and downloads the appropriate driver when necessary; an activation phase that loads the device driver and registers the medical devices; and an execution phase that is responsible for tracking the medical devices' heartbeats and gathers and transmits data to and from the medical devices.

A driver library 250 may store a plurality of drivers that may be used and installed on particular devices, when required. Further, a device message routing component 252 handles routing messages from source to destination across the device messaging services 212. Messages may take on a variety of forms, and may contain vastly different types of content. Various types of messaging may include request and reply messaging, publish and subscribe messaging, and asynchronous one-way messaging. Request and reply messaging includes taking a message from a source, routing it to a single destination, and routing a reply message from the destination back to the original source. Publish and subscribe messaging involves a publisher sending messages out on a named topic, which may be received by multiple subscribers. Asynchronous one-way messaging includes doing requests and reply messaging without needing to receive a reply. The only receipt message may be an indication that the message was successfully sent.

With continued reference to FIG. 2, application services 214 includes various components, including healthcare service providers 254, a database 256, system services 260, and an application 268. The system services 260 may consume some or all of the information that the main bus 246 provides. In some instances, the system services 260 may be application programming interfaces (APIs), which may support requests made by computer programs, such as applications. For instance, the system services 260 may use the main bus 246 to determine where a connected device is located. The application services 214 may include various components that may all utilize information sent by the main bus 246. These may include, for example, an aggregation component 262, a data store 264, and a patient to device association 266, which is further discussed herein. The aggregation component 262 allows for a user to query a patient by a patient identification over a large number of patient identifications. Once a match is found, information relating to that patient, such as devices that the patient is associated with, may be retrieved. The data store 264 stores data that is published by the medical devices.

In various embodiments of the present invention, the system services 260 run on the main bus 246, and thus together with the main bus 246, may provide additional functionality to the system as a whole. For example, when various system services 260 run on the main bus 246, the main bus 246 may store discrete data posts, such as heart rate, systolic blood pressure, diastolic blood pressure, etc., in a data store, such as data store 264, for historical queries and archiving. Further, the main bus 246 may chart acquired discrete data into a patient's EMR; publish medical device outcomes, such as lab results and other test results, to a patient's EMR; and publish digital media from a device into a patient's EMR, publish infusion data, if required, and infusion events (e.g., infusion rate, volume infused, volume to be infused, rate change, begin bag, end bag) into a patient's EMR.

The application 268 works with the system services 260 to facilitate specific functionality, such as a patient to device association. The application 268, in one embodiment, may be a user interface. For example the user interfaces may be screen shots of associating a patient to a device, or to an order, or screen shots of associating a patient with a particular healthcare provider. While one application 268 is illustrated in FIG. 2, more than one application is considered to be well within the scope of the present invention. The system services 260 and the application 268 are incorporated such that the system services 260 retrieve raw data from the main bus 246 and other components, while the application 268 uses that information and presents it to a user through a user interface.

While only a main bus 246 is illustrated in FIG. 2, more than one bus may be used in implementing embodiments of the present invention. By way of example only and not limitation, the main bus 246 may be a first bus that is responsible for managing all of the medical devices. This main bus 246 may be located at the facility, such as a hospital. One or more local busses may be present that can store and facilitate the transfer of information from one or more medical devices, and that transfer that information to the main bus 246. The main bus 246 may not even be aware that there are local busses, as the local busses may just be proxying messages that they receive from the medical devices. Local busses may also be present at the facility (e.g., hospital), but may be physically located in a patient's room, for example, such as on a cart where an associated medical device is located. In one embodiment of the present invention, more than one main bus 246 may be available to provide a backup system. One main bus may be a primary node, and the other may be a secondary node. If one node goes down, the secondary node may be utilized. Additionally, the nodes or busses may be used in conjunction with one another such that each has certain responsibility, for example.

The database 256, in one embodiment, may be sent patient, medical device, and order association information. For instance, identification of a patient and medical device that have been associated may be sent to the database 256. Any data that it released by the medical device may also be routed to the database 256 so that this information can be stored in a flowsheet, for example. A clinician may then make the decision as to what to do with the data. For example, the clinician may decide that certain data points should be included in the patient's chart, and the others may be completely deleted from the database 256. A specific example of this may be when a clinician looks at data in the database 256 that is associated with a certain patient. The data may include values at different times, such as 12:00 PM, 12:15 PM, and 12:30 PM. The clinician may not wish for all of these values to be entered into the patient's chart, but may choose, for example, just the 12:00 PM and 12:30 PM entries to officially document. Additionally, having this information in the database 256 allows for a higher accuracy. In one instance, a clinician may write down in a patient's chart that an infusion pump began at 12:10 PM, when it actually started at 12:06 PM. Having this information in the database 256 allows for the clinician to officially document accurate start and end times, as well as other values whose accuracy is important to the patient's health.

As previously discussed, various healthcare service providers 254 may wish to receive data or information regarding a particular medical device or patient. In this case, the adapters 240 may be configured to send this information via an HL7 or ASTM connection, for example, to the healthcare service providers 254. In one embodiment, the system services 260 may communicate with various healthcare service providers 254, and this communication takes place via the main bus 246.

Figure 3:
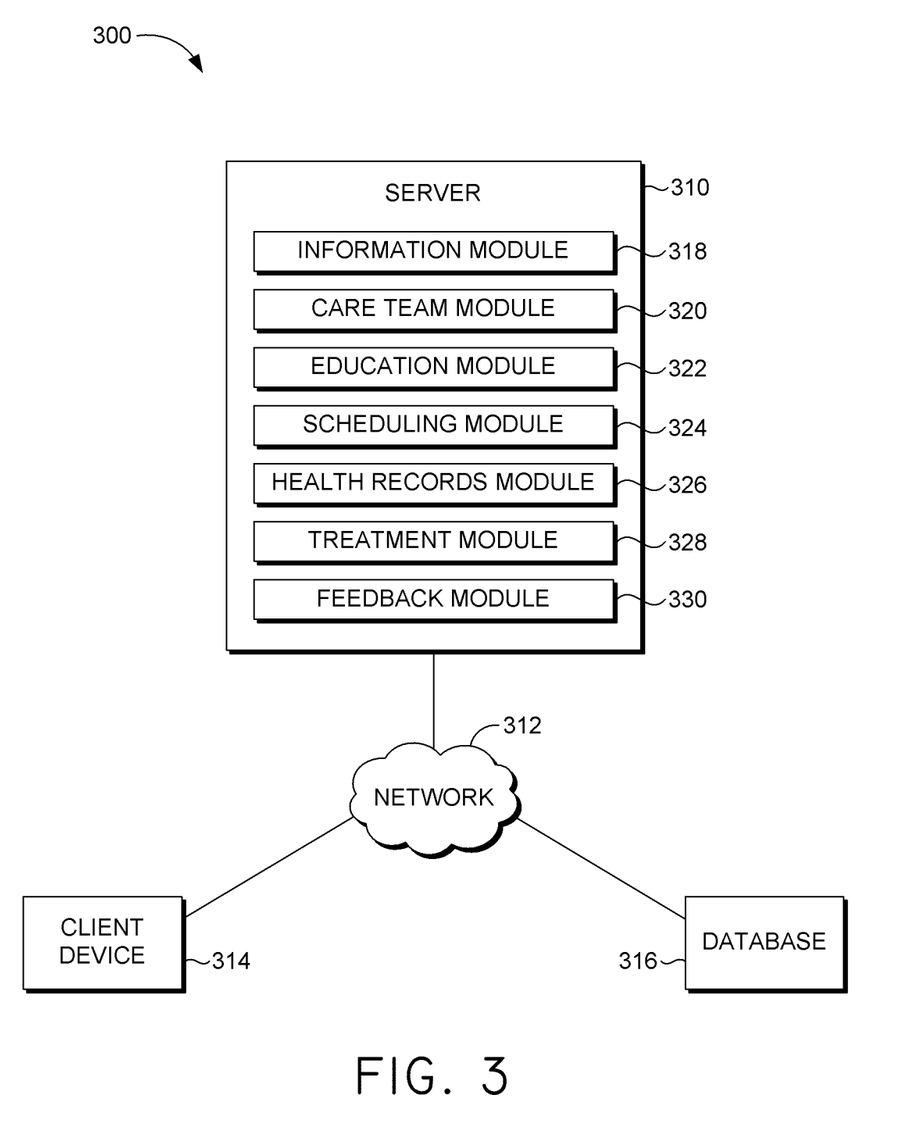
FIG. 3 is a block diagram of an exemplary system, according to an embodiment of the present invention.

Turning now to FIG. 3, a block diagram of an exemplary system is shown, in accordance with an embodiment of the present invention, designated generally as reference numeral 300. System 300 includes a server 310, a network 312, a client device 314 and a database 316. Server 310 includes and may operate a set of modules, 318, 320, 322, 324, 326, 328 and 330. Server 310 may communicate with client device 314 by way of network 312 to provide interactive in-patient experience. Server 310 may retrieve data via network 312 from database 316. Database 316 may include data received from one or more medical devices, data published by the bus, and data transferred from a patient's electronic medical record (EMR).

The set of modules 318, 320, 322, 324, 326, 328 and 330 may communicate with client device 314 to present via a user interface various forms of information to the patient. Server 310 may include an information module 318, for providing the patient or the patient's family with information about the healthcare facility. For instance, information module 318 may provide information such as the mission statement of the healthcare facility, a welcome video, and provide of list of amenities available to patient. Information module 318 may also provide maps and other directional information to enable patients to find their way around the healthcare facility. Additionally, the information module 318 may provide patients with information about the geographical area surrounding the healthcare facility, such as local events and venues for food and lodging.

Care team module 320 may provide the patient or the patient's family with information about the people designated to care for the patient throughout their stay at the healthcare facility. For example, care team module 320 may provide information such as the name, position, picture and personal and professional biography of the healthcare providers that interact with the patient during their hospital stay. When a patient is admitted, discharged or transferred within the healthcare facility, the care team module may initiate a servlet to obtain information about the healthcare providers associated with the admission, discharge or transfer of the patient. Alternatively, the care team module may automatically associate a healthcare provider to the care team of all patient or allow manual association of a healthcare provider to a patient. The care team module may also facilitate the creation and updating of healthcare provider profiles containing the healthcare providers information. In one example, the care team module may associate a particular healthcare provider with the care team of a patient when the healthcare provider accesses the patient's medical chart in the EMR. The care team module 320 may also be associated with an indoor positioning system to track the physical locations of the patient's healthcare providers. Additionally, care team module 320 in association with the indoor positioning system may enable a patient to request biography information about a healthcare provider based on a healthcare provider's name or picture and may provide information such as a name, a position and a picture of the healthcare provider, when the healthcare provider enters a patient's room.

Education module 322 may provide the patient with health education information. For instance, education module 322 may enable a patient to retrieve electronic documents related to their illness or course of treatment. Alternatively, education module 322 may provide interactive education tutorials for the patient. Additionally, education module 322 may allow a patient post questions in response the retrieved electronic documents or interactive tutorials, and alert a member of the patient's healthcare team about the patient's concerns. The education module may also keep track of when a patient has competed a health education information learning activity such as retrieving an electronic document or completing an interactive tutorial.

Scheduling module 324 may provide patients with a representation of their specific events and/or a task list for the day. The events populated on the patient's schedule may include scheduled test, standard food service times, chapel services and hospital events. In addition to the schedules events, scheduling module 324 may provide the patient with a patient-specific task list. For example, the task list may include instructions for the patient related to their treatment or education such as designated patient education tutorials and required or recommended exercises.

Health records module 326 may enable a patient to access information regarding their personal care. For example, module 326 may enable patient to access portions of their Personal Health Record and update pertinent information. Module 326 may access the healthcare facility's records keeping system and determine via parameters set by a healthcare provider, the portions of a patient's EMR accessible by a patient. The heath records module 326 may also allow the patient to edit select portions of their EMR. For example health records module 326 may enable a patient to update information relating to allergies or update emergency contact information. Additionally, the health records module 326 may allow a patient to communicate with their physician or member of their care team.

Treatment module 328 may provide real-time information from medical devices associated with the patient. Treatment module 328 may retrieve the information from a bus associated with the medical devices or from data published from the devices to database 316. The bus associated with treatment module 328 may be similar to the bus previously described with reference to FIG. 2.

Feedback module 330 may allow patients to provide real-time opinion information regarding their stay at the healthcare facility. The feedback module 330 may solicit input from the patient via quality of care surveys. Module 330 may include instant feedback notices to allow the healthcare providers and healthcare facility to take immediate action regarding an issue and work to improve the overall patient experience. The notification component of the feedback module may include an escalation and relay measure, which alerts the healthcare providers when the results of a patient feedback survey fall below a satisfactory level. The feedback module 330 allows the management of the healthcare facility to target specific areas for feedback regarding new protocols or processes. Feedback module 330 may eliminate the delays often associated with standard written survey results.

Figure 4:
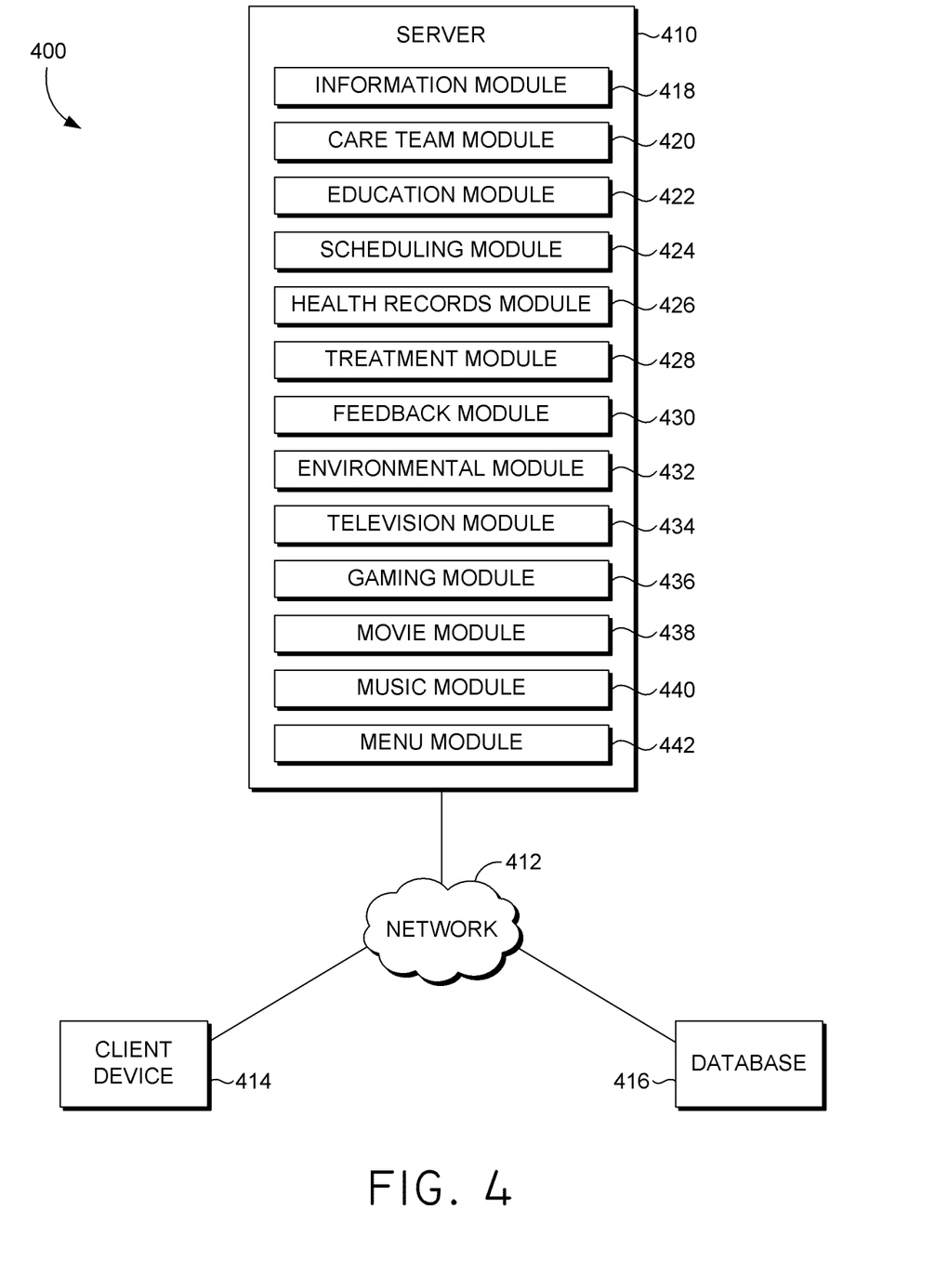
FIG. 4 is a block diagram of an exemplary system, according to an embodiment of the present invention.

Referring now to FIG. 4, a block diagram of an exemplary system, according to an embodiment of the present invention is illustrated and designated generally as reference numeral 400. System 400 includes a server 410, a network 412, a client device 414 and a database 416. Server 410 includes and may operate a set of modules, 418, 420, 422, 424, 426, 428, 430, 432, 434, 436, 438, 440, and 442. Server 410 may communicate with client device 414 by way of network 412 to provide interactive in-patient experience. Server 410 may retrieve data via network 412 from database 416. Database 416 may include data received from one or more medical devices, data published by the bus, and data transferred from a patient's electronic medical record (EMR).

As previously described in relation to FIG. 3, the set of modules may include an information module 418, a care team module 420, an education module 422, a scheduling module 424, a health records module 426, a treatment module 428 and a feedback module 430. The set of modules may also include an environmental module 432. Environmental module 432 may allow the patient, a care provider or the family members and/or friends of the patient to control the environmental conditions of the patient's room. For instance, the environmental module 432 may enable a patient to adjust the lighting setting in a room. Alternately, module 422 may allow a patient to control the temperature of his or her room.

The set of modules may also include a television module 434, a gaming module 436, a movie module 438, a music module 440 and a menu module 442. The television module 434 may provide television services to the patient. For example the television module may facilitate a patient's ability to pause/rewind or record live television. Additionally, a healthcare provider and/or a parent of a patient may control via module 434 the times when television services are available to the patient and the type of programming accessible by the patient.

The gaming module 436 may provide an interactive gaming experience for the patient. For example, the module 436 may facilitate gaming though externally connected gaming systems of built-in computer based games. The movie module 438 may provide movies to the patient. The module 438 may provide the movies upon the demand of the patient. As with the television module 434 a healthcare provider and/or a parent of a patient may control via module 438 the times when movies are available to the patient and the type of movie content accessible by the patient.

The music module 440 may provide music upon the demand of the patient. The module 440 may provide a music library that can be accessed via the client device 414. Care providers may control via the music module 440 the time when the patient is allowed to access the music content. For instance, patients may be prohibited from accessing music content during scheduled quiet periods.

The menu module 442 may provide patients with access to the food service system of the healthcare facility as well as the restaurants of the healthcare facility. The menu module may also provide access to the gift shops associated with the healthcare facility.

Figure 5:
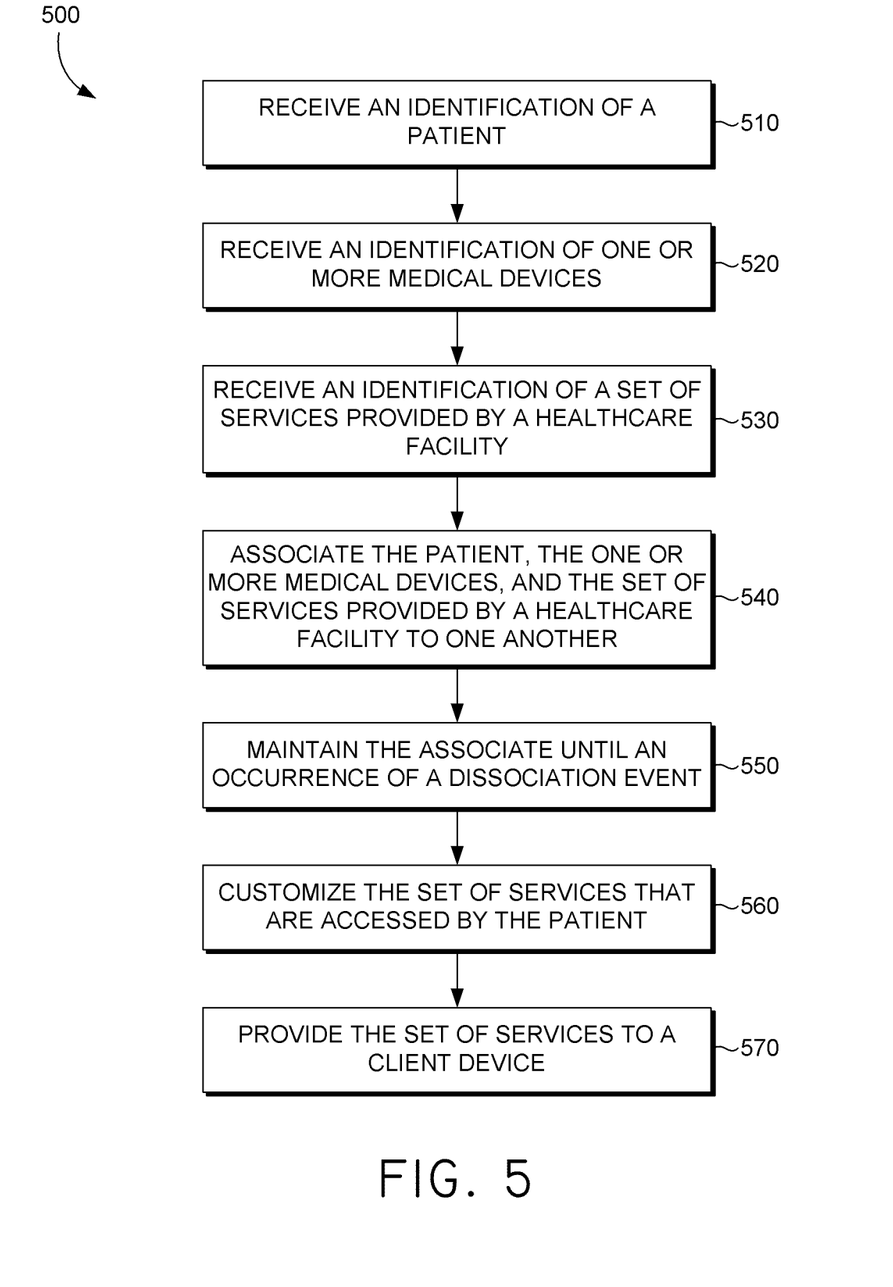
FIG. 5 is an illustrative flow diagram of a method for providing an interactive healing environment to a patient in a healthcare facility, in accordance with an embodiment of the present invention.

FIG. 5 is an illustrative flow diagram 500 is shown of a method for providing an interactive healing environment to a patient, in accordance with an embodiment of the present invention. Initially, an identification of a patient is received at step 510. A patient's identification may be received in one of many ways. For exemplary purposes only and not limitation, a patient may be identified by scanning a barcode located on or near the patient. Alternatively, an identification corresponding to the patient (e.g., identification number, patient's name) may be entered into a computer device, such as a PDA or some other type of portable computing device). In one aspect of the present invention, a database containing a plurality of patient identifications may be searched by a user to locate a particular patient. The database may contain only those patients located in a certain portion of a hospital, or may contain a broader range of patients, such as any that have been checked into the hospital, for example. Further, the database, in one embodiment, is an electronically searchable database.

At step 520, an identification of a medical device is received. Medical device identification may be received in the same way as patient identifications, as outlined above. For example, a barcode associated with the device may be scanned, identification information for the device may be entered into a computing device, a device may be searched for in a database, or the like. At step 530, an identification of a set of healthcare services provided by a healthcare facility is received. The set of healthcare services may relate to the in-patient's treatment, and may include diagnostic tests, and therapies that are patient specific. Identification of the patient specific healthcare services may be received in the same way as patient identifications, as outlined above. For example, a barcode associated with a particular healthcare service may be scanned, identification information for the healthcare service may be entered into a computing device, a healthcare service may be searched for in a database, or the like.

In response to receiving the identifications of the patient, the medical devices, and the healthcare facility service, the patient, medical device and healthcare service may be associated to one another at step 540. Once an association has been formed between the patient, the medical device, and the healthcare service, data from the medical device may be continuously routed to a data store, where associations and related data are stored. At step 550, the association or the patient, the medical device and the healthcare service is maintained until the occurrence of a dissociation event. While the association is maintained, as previously mentioned, data from the medical device may be continuously routed and saved in a data store, such as, for example, data store 264 in FIG. 2. Data routed from the medical devices to the data store may be routed by a bus, such as main bus 246, also in FIG. 2.

In one embodiment, a disassociation event may occur by a clinician disassociating the device from a patient (e.g., selecting the device by scanning it or selecting the checkbox, and selecting a disassociate button on a screen display). This may also be done by the selection of a patient and a device (e.g., selected by scanning a barcode or selecting a checkbox), followed by a clinician selecting a disassociate button on a screen display. Alternatively, more than one device may be disassociated at the same time. As previously described, a select all button may be available if it is desired that all of the devices be selected.

In another embodiment, an indication may be received that a device that is currently associated to a patient has gone offline. As used herein the term, "online" indicates a state of connectivity between a device and a patient, while "offline" indicates a disconnected state between a device and the patient. One mechanism for determining whether a device is online or offline is a device heartbeat, which is described in relation to FIG. 2. A device heartbeat is a message sent from the device to device messaging services 212 in FIG. 2, for example, that indicates that the device is online. If this device heartbeat is not received for a certain, and perhaps predetermined period of time, it may be determined that the device is offline.

In yet another embodiment, a user (e.g., clinician) may choose to override an existing association between another patient and a medical device so that a new patient is associated with the device. If the user chooses to override the existing association, that association will be terminated in favor of a new association with a new patient.

At step 560, the set of system services that are accessed by the patient are customized. The set of system services enable the patient to interact with a set of modules. As described in relation to FIGS. 3 and 4, the set of modules may include an information module, a care team module, an education module, a scheduling module, a health records module, a treatment module, and a feedback module. In response to customizing the set of system services accessible by the patient, the set of system services is provided to a client device at step 570. The client device enables the patient to retrieve and/or input information by using the set of customized system services interacting with the set of modules of the control server 22.

Figure 6:
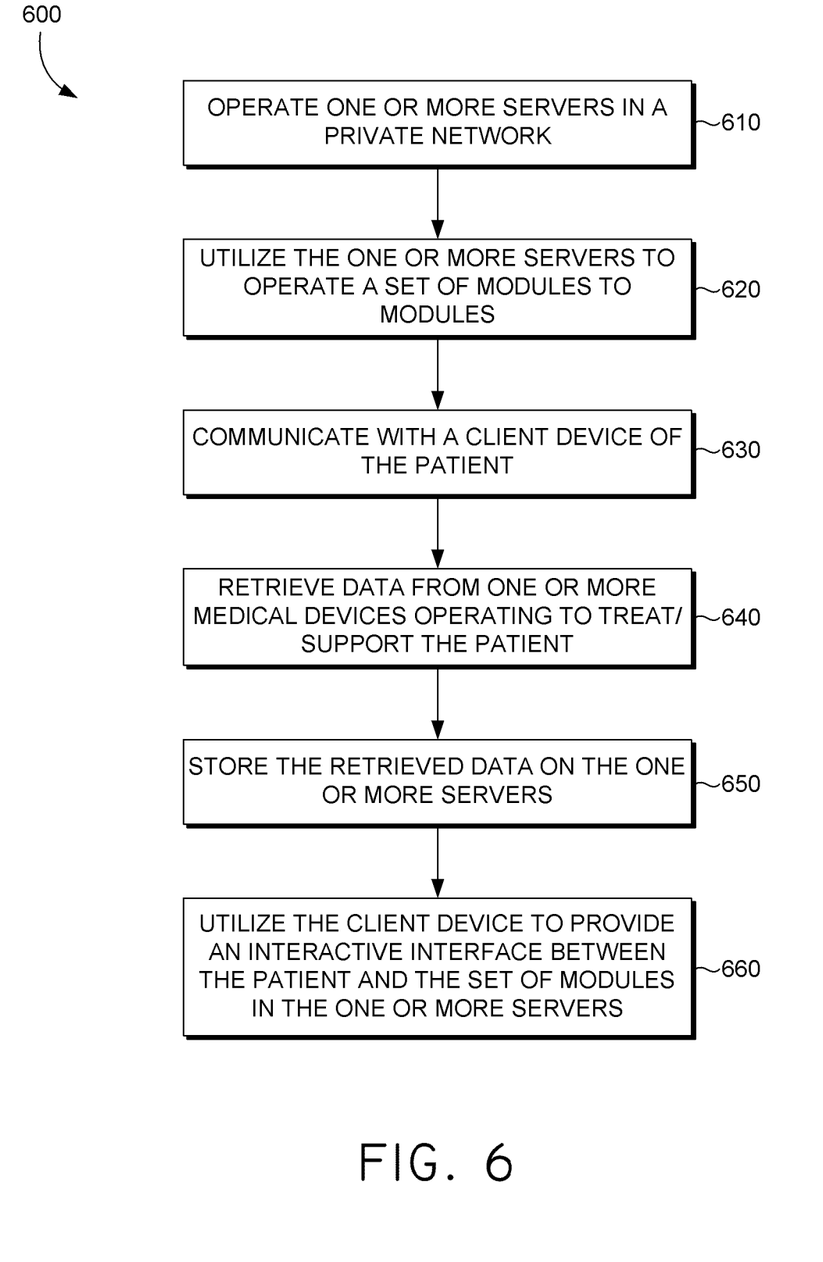
FIG. 6 is an illustrative flow diagram of a method for providing an interactive healing environment to a patient in a healthcare facility, in accordance with an embodiment of the present invention.

Turning to FIG. 6, an illustrative flow diagram 600 is shown of a method for providing an interactive healing environment to a patient, in accordance with an embodiment of the present invention. Initially, a control sever (not shown) is operated in a private network at step 610. At step 620, the control server is utilized to operate a set of modules. As described in relation to FIGS. 3 and 4, the set of modules may include an information module, a care team module, an education module, a scheduling module, a health records module, a treatment module, and a feedback module. At step 630, the control server communicates with a client device of the patient. The client device enables the patient to retrieve and/or input information by using the set of customized system services interacting with the set of modules of the control server 22. At step 640, the control server retrieves data from one or more medical devices. As previously describe, the medical devices may be used to treat or support the patient and may be associated with the patient via a bus as described in relation to FIG. 2. At step 650 the retrieved data is stored on the control server. The control server then utilizes the client device to provide an interactive interface between the patient and the set of modules of the control server, at step 660.

It will be understood that certain features and sub-combinations of utility may be employed without reference to features and sub-combinations and are contemplated within the scope of the claims. Furthermore, the steps performed need not be performed in the order described.

The invention claimed is:

1. A system for providing an interactive healing environment to a patient in a healthcare facility, comprising:

one or more servers configured to operate in a private network wherein each server has a processor coupled to a memory;

the one or more servers configured to operate a set of modules to communicate through a computer network via a bus component with a client device of the patient and with one or more medical devices associated with the patient, wherein the set of modules includes:

an information module that provides a set of information about the healthcare facility;

a care team module that provides a set of information about a set of people who give care to the patient in the healthcare facility;

an education module that provides at least one of a health education information, an electronic document retrieval, and an interactive patient education;

a scheduling module that provides at least one of a schedule for the patient and a task list for the patient;

a health records module that provides the patient access to at least one of their personal care information and their personal health record;

a treatment module that provides real-time information from the one or more medical devices associated with the patient;

wherein the one or more servers are further configured to retrieve data from the one or more medical devices via the bus component including an identification of the patient, an identification of the one or more medical devices associated with the patient and an identification of a set of healthcare services provided by the healthcare facility, wherein the one or more medical devices operate to treat the patient or operate to support the patient;

wherein the one or more servers are further configured to associate the identification of the patient, the one or more medical devices, and the set of healthcare services provided by the healthcare facility to one another for a period of time determined by a treatment of the patient in the healthcare facility and continuously receive data from the one or more medical devices for a period of time that the one or more medical devices is connected to the bus component, wherein the one or more servers maintain a patient to medical devices association between the identification of the patient and the one or more medical devices until an occurrence of a disassociation event is detected by the bus component, wherein the one or more medical devices is connected to the bus component and the patient to medical devices association is maintained during a period of time in which a device heartbeat of the one or more medical devices is detected by the bus component, wherein the disassociation event is detected when the device heartbeat of the one or more medical devices is not detected for a predetermined period of time;

wherein the one or more servers are further configured to transmit a notice of a disconnect event in response to the one or more medical devices deregistering or disconnecting from the bus component and configured to terminate sending of the device heartbeat of the one or more medical devices that are deregistered or disconnected; and the client device configured to operate to provide an interactive interface between the patient and the set of modules in the one or more servers.

2. The system of claim 1 wherein the set of modules further includes at least one of:
a television module that provides television services;
a gaming module that enables an interactive gaming experience;
a movie module that provides a first on-demand selection of video content;
a music module that provides a second on-demand selection of audio content; and
a menu module that provides an access to food services and gift shops associated with the healthcare facility.

3. The system of claim 1, wherein the disassociation event includes one or more of a disassociation by a clinician, an indication that the one or more medical devices is offline, or an override caused by an association of another patient to the one or more medical devices.

4. The system of claim 1, wherein one or more of the identification of the patient, or the identification of the one or more medical devices are received by scanning a barcode that is associated with the patient, or the one or more medical devices.

5. The system of claim 1, wherein one or more of the identification of the patient, or the identification of the one or more medical devices are received by a user selection of the identification of the patient, or one or more medical devices identification found in an electronically searchable database that contains a plurality of identifications.

6. The system of claim 1, wherein the care team module is associated with an indoor positioning system to track physical locations of the set of people who give care to the patient in the healthcare facility and wherein the care team module provides information including one or more of a name, position and a picture of a healthcare giver, when the healthcare giver enters a patient room.

7. The system of claim 1, wherein the education module is configured to monitor when the patient has completed a health education information learning activity and further comprising the one or more servers configured to update an electronic medical record associated with the patient when the patient has completed the health education information learning activity.

8. The system of claim 1, further comprising a feedback module configured to solicit feedback information from the patient regarding their treatment at the healthcare facility, wherein the feedback information comprises a response of the patient to one or more quality of care surveys.

9. The system of claim 8, further comprising the one or more servers configured to alert a healthcare facility management team and the set of people who give care to the patient when positive feedback information provided by the patient falls below a predetermined threshold.

10. A system for providing an interactive healing environment to a patient in a healthcare facility, comprising:
one or more servers configured to operate in a private network, wherein each server has a processor coupled to a memory;
the one or more servers configured to operate a set of modules that communicate through a bus with a client device of the patient, the client device has a processor coupled to a memory, wherein the bus maintains an association between the patient and the client device even when the client device is disconnected, and the bus maintains the association until an occurrence of a disassociation event, and wherein the set of modules includes:
an information module that informs the patient about the healthcare facility and a set of services in the healthcare facility;
a care team module that provides a set of information about a set of people who give care to the patient in the healthcare facility;
an education module that provides at least one of a health education information, an electronic document retrieval, and an interactive patient education;
a scheduling module that provides at least one of a schedule for the patient and a task list for the patient;
a health records module that provides the patient access to at least one of their personal care information and their personal health record; and
a treatment module that retrieves real-time information through the bus from one or more medical devices associated with the patient and provides the real-time information through the bus to the client device of the patient, wherein a medical device has a processor coupled to a memory;
wherein the one or more servers are configured to retrieve data from the one or more medical devices associated with the patient, wherein the one or more medical devices operate to treat the patient or operate to support the patient;

wherein the one or more servers are configured to maintain a patient-to-medical devices association between an identification of the patient and the one or more medical devices until the occurrence of the disassociation event is detected by the bus, wherein the one or more medical devices is connected to the bus and the patient to medical devices association is maintained during a period of time in which a device heartbeat of the one or more medical devices is detected by the bus, wherein the disassociation event is detected when the device heartbeat of the one or more medical devices is not detected for a predetermined period of time;

wherein the one or more servers are further configured to transmit a notice of a disconnect event in response to the one or more medical devices deregistering or disconnecting from the bus based on at least the disassociation event and to terminate sending of the device heartbeat of the one or more medical devices that are deregistered or disconnected; and the client device configured to provide an interactive interface between the patient and the set of modules in the one or more servers.

11. The system of claim 10, wherein the set of modules further includes at least one of:
a television module that provides television services;
a gaming module that enables an interactive gaming experience;
a movie module that provides a first on-demand selection of video content;
a music module that provides a second on-demand selection of audio content; and
a menu module that provides an access to food services and gift shops associated with the healthcare facility.

12. The system of claim 11, further comprising a feedback module configured to solicit input from the patient to correct and improve a stay of the patient in the healthcare facility.

13. The system of claim 10, wherein the care team module is associated with an indoor positioning system to track physical locations of the set of people who give care to the patient in the healthcare facility and wherein the care team module is configured to provide information including a name, a position and a picture of a healthcare giver, when the healthcare giver enters a room of the patient.

14. The system of claim 10, wherein the education module is configured to monitor when the patient has completed a health education information learning activity.

15. The system of claim 13, wherein the health records module is configured to update an electronic medical record, associated with the patient, in a healthcare recordkeeping system when the patient completes a health education information learning activity.

16. The system of claim 10, further comprising a feedback module configured to solicit feedback information from the patient regarding their treatment at the healthcare facility, wherein the feedback information comprises a response of the patient to one or more quality of care surveys.

17. The system of claim 16, further comprising a notification component configured to alert a healthcare facility management team and a healthcare provider when positive feedback information provided by the patient falls below a pre-determined threshold.

18. The system of claim 10, further comprising an environmental module configured to allow the patient and the set of people who give care to the patient to control environmental conditions in a room of the patient, wherein the environmental conditions include lighting and temperature.

19. One or more non-transitory computer-readable storage media having computer-executable instructions embodied thereon, that, when executed perform a method for providing an interactive healing environment to a patient, the method comprising:
operating one or more servers in a private network, wherein each server has a processor coupled to a memory;
utilizing the one or more servers to operate a set of modules, wherein the set of modules communicates through a bus with a client device of the patient, the client device has a processor coupled to a memory, the bus maintains an association between the patient and the client device even when the client device is disconnected, the bus maintains the association until an occurrence of a disassociation event, and wherein the set of modules includes:
an information module that provides a set of information about a healthcare facility to the patient;
a care team module that provides a set of information about a set of people who give care to the patient in the healthcare facility;
an education module that provides at least one of a health education information, an electronic document retrieval, and an interactive patient education;
a scheduling module that provides at least one of a schedule for the patient and a task list for the patient;
a health records module that provides the patient access to their personal care information and their personal health record; and
a treatment module that retrieves real-time information through the bus from one or more medical devices associated with the patient and provides the real-time information through the bus to the client device of the patient, wherein a medical device has a processor coupled to a memory;
retrieving data from the one or more medical devices associated with the patient, wherein the one or more medical devices operate to treat the patient or operate to support the patient;
storing the retrieved data on the one or more servers;
maintaining a patient-to-medical devices association between an identification of the patient and the one or more medical devices until the occurrence of the disassociation event is detected by the bus, wherein the one or more medical devices is connected to the bus and the patient to medical devices association is maintained during a period of time in which a device heartbeat of the one or more medical devices is detected by the bus, wherein the disassociation event is detected when the device heartbeat of the one or more medical devices is not detected for a predetermined period of time;
transmitting a notice of a disconnect event in response to the one or more medical devices deregistering or disconnecting from the bus based on at least the disassociation event and terminating sending of the device heartbeat of the one or more medical devices that are deregistered or disconnected; and
utilizing the client device to provide an interactive interface between the patient and the set of modules in the one or more servers.

20. The one or more non-transitory computer-readable storage media of claim 19, further comprising a feedback module configured to solicit input from the patient to correct and improve a stay of the patient in the healthcare facility.

\* \* \* \* \*